United States Patent [19]
Snelling et al.

[11] 4,447,145
[45] May 8, 1984

[54] CHARGED PARTICLE SENSOR

[75] Inventors: Christopher Snelling, Penfield; Dusan G. Lysy, Fairport, both of N.Y.

[73] Assignee: Xerox Corporation, Stamford, Conn.

[21] Appl. No.: 373,477

[22] Filed: Apr. 30, 1982

[51] Int. Cl.³ .................................... G03G 15/08
[52] U.S. Cl. ........................ 355/14 D; 355/3 DD; 430/30; 430/120; 118/691
[58] Field of Search ............... 355/3 DD, 14 D; 324/452, 457, 71.4; 204/299 R; 222/DIG. 1; 118/689, 691, 624, 644, 653, 657, 658, 665, 668; 430/30, 120; 356/121, 126, 239

[56] References Cited

U.S. PATENT DOCUMENTS

| | | | |
|---|---|---|---|
| 2,304,814 | 12/1942 | Glasser | 356/126 |
| 3,578,975 | 5/1971 | Wheeler | 356/126 X |
| 3,635,373 | 1/1972 | Kuhl et al. | 222/DIG. 1 X |
| 3,757,999 | 9/1973 | Maksymiak | 222/DIG. 1 X |
| 3,783,270 | 1/1974 | Kamachi | 356/126 X |
| 3,918,818 | 11/1975 | Giles | 356/239 |
| 4,111,151 | 9/1978 | Ruckdeschel | 355/14 D X |
| 4,195,260 | 3/1980 | Sakamoto et al. | 355/3 DD X |
| 4,226,525 | 10/1980 | Sakamoto et al. | 355/14 D X |
| 4,273,843 | 6/1981 | Fujita et al. | 355/3 DD X |

*Primary Examiner*—A. C. Prescott

[57] ABSTRACT

An apparatus in which the developability of electrostatically charged particles in a mixture of particulate material is measured. The apparatus includes a pair of spaced-apart conductive plates through which at least a portion of the particulate mixture flows. One of the plates is transparent with a member being secured thereto. The transparent plate is electrically biased to attract charged particles thereto. A beam of energy is transmitted through the transparent plate and member. The intensity of the internally reflected beam is detected to provide a measurement of the quantity of charged particles adhering to the transparent plate.

28 Claims, 6 Drawing Figures

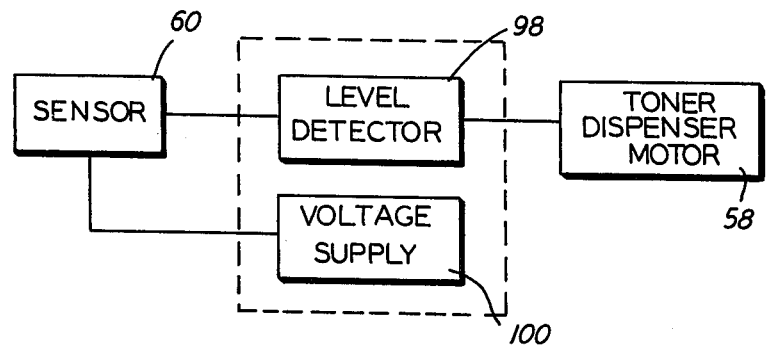
FIG. 2
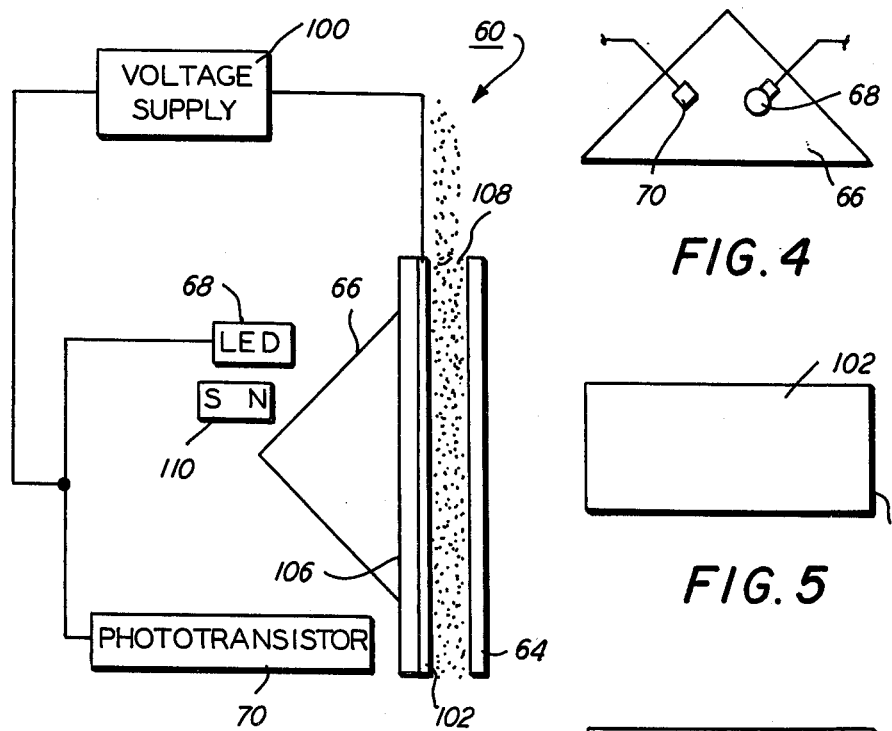
FIG. 3
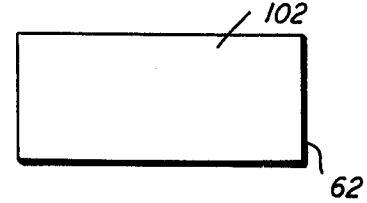
FIG. 4
FIG. 5
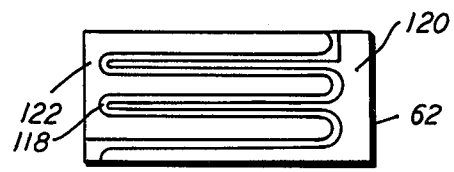
FIG. 6

CHARGED PARTICLE SENSOR

This invention relates generally to an electrophotographic printing machine, and more particularly concerns an apparatus for sensing electrostatically charged particles in a mixture of particulate material.

Generally, the process of electrophotographic printing includes charging a photoconductive member to a substantially uniform potential so as to sensitize the surface thereof. The charged portion of the photoconductive surface is exposed to a light image of an original document being reproduced. This records an electrostatic latent image on the photoconductive member corresponding to the informational areas contained in the original document. After the electrostatic latent image is recorded on the photoconductive member, the latent image is developed by brining a developer mixture into contact therewith. This forms a powder image on the photoconductive membe which is subsequently transferred to a copy sheet. Finally, the powder image is heated to permanently affix it to the copy sheet in image configuration.

A common type of developer mixture frequently used in electrophotographic printing machines comprises carrier granules having toner particles adhering triboelectrically thereto. This two-component mixture is brought into contact with the photoconductive surface. The toner particles are attracted from the carrier granules to the latent image. During usage, toner particles are depleted from the developer mixture and must be periodically replenished therein. Heretofore, the concentration of toner particles in the developer mixture was controlled within a pre-selected bandwidth. However, in an electrophotographic printing machine, it is desirous to achieve optimum developability rather than merely maintaining the concentration of toner particles within the developer mixture at a substantially constant level. In order to optimize developability, the output density of the copy should correspond substantially to the input density of the original document. In order to achieve this, it is necessary to regulate the developability of the developer mixture. Developability is related to environmental conditions such as temperature and humidity, as well as the concentration of tone particles in the developer material. Other physical parameters of the development system also affect developability, for example, spacing, electrical bias, mass flow rate, and the magnetic field pattern, amongst others. In addition, many other factors such as state of compaction of the developer material, the charge on the toner particles and carrier granules, as well as the state of attraction of the toner particles to the carrier granules all influence developability. Thus, in order to truly regulate developability to optimize the resultant copy, development of the latent image must be simulated.

Various techniques have been devised for measuring the concentration of toner particles within a developer mixture. The following disclosures appear to be relevant: U.S. Pat. No. 3,376,854, Patentee: Kamola, Issued: 1968; U.S. Pat. No. 3,635,373, Patentee: Kuhl et al., Issued: 1972; U.S. Pat. No. 3,757,999, Patentee: Maksymiak, Issued: 1973; Co-Pending U.S. patent application Ser. No. 349,107, Applicant: Snelling, Filed: 1982.

The relevant portions of the foregoing disclosures may be briefly summarized as follows:

Kamola describes a toner concentration control system wherein two parallel spaced conductive plates define a channel through which developer material passes. One plate has a pattern thereon which is electrically biased to attract the toner particles from the developer mixture. A light source and photocell are positioned within the plate interposed therebetween. Another photocell is arranged as a leg of a wheatstone bridge circuit which includes the first photocell. In this manner, an unbalance of the bridge circuit causes toner particles to be dispensed to the developer mixture.

Kuhl et al. discloses a system employing two parallel spaced conductive plates through which the developer mixture flows. The plates are connected to a circuit wherein each is electrically charged alternately for equal periods of time to attract and repel toner particles. A light source is located on one side of the two plates with the photocell being located on the other side to sense the illumination intensity transmitted therethrough. The photocell develops an electrical signal which is processed to form an error signal. The error signal controls the dispensing of toner particles into the developer mix.

Maksymiak teaches the use of spaced conductive plates alternately electrically charged between which the developer mixture flows. A light source is positioned on one side of the two plates and a photocell on the other side thereof. In this way, the intensity of the light rays passing therethrough is detected. The system also provides a measurement of the toner particle concentration within the developer mix.

Snelling discloses a substantially tansparent prism having an electrically conductive layer on one surface thereof electrically biased to attract toner particles from a developer roller. A light source transmits light rays through the prism onto the toner particles attracted thereto. The internally reflected light rays are detected by a photosensor.

In accordance with one aspect of the present invention, there is provided an apparatus for sensing electrostatically charged particles. The apparatus includes a pair of spaced-apart electrically conductive plates defining a passageway through which a portion of the charged particles flow. At least one of the pair of plates is transparent. A member is secured to one surface of the transparent plate. Means electrically bias the transparent plate to attract a portion of the charged particles to the other surface thereof. Means are provided for tansmitting a beam of energy through the member and plate. Means detect the intensity of the beam of energy internally reflected through the member and transparent plate.

Pursuant to another aspect of the present invention, there is provided an electrophotographic printing machine of the type having an electrostatic latent image recorded on a photoconductive surface. The latent image is developed with charged particles from a developer mixture. A pair of spaced-apart electrically conductive plates define a passageway through which a portion of the developer mixture flows. At least one of the plates is substantially transparent. A member is secured to one surface of the transparent plate. Means electrically bias the transparent plate to attract a portion of the charged particles to the other surface of the transparent plate. Means are provided for transmitting a beam of energy through the member and plate. Means detect the intensity of the beam internally reflected through the plate and member.

Other features of the present invention will become apparent as the following description proceeds and upon reference to the drawings, in which:

FIG. 2 is a block diagram of a control system used to regulate the developability of the developer mixture employed in the FIG. 1 printing machine;

FIG. 3 is a schematic elevational view of the sensing circuitry associated with the FIG. 2 control system;

FIG. 4 is a schematic elevational view showing a preferred embodiment of the prism, light source and light sensor of the FIG. 3 circuitry;

FIG. 5 is a schematic plan view of the FIG. 3 transparent plate depicting one embodiment of the pattern of conductive material adhering to the surface of the plate; and FIG. 6 is a schematic plan view of the FIG. 3 transparent plate depicting another embodiment of the pattern of conductive material adhering to a surface thereof.

Figure 1:
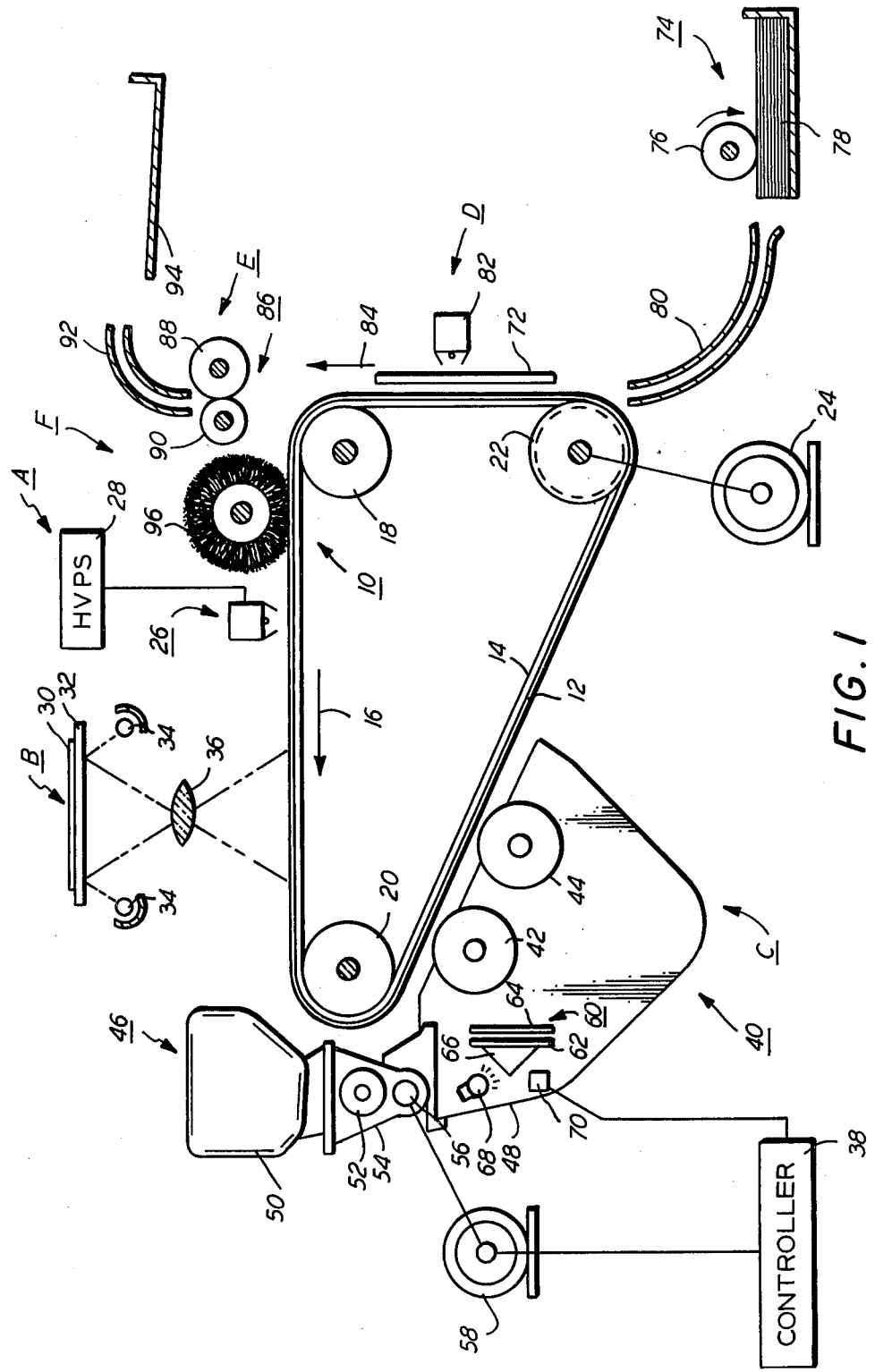
FIG. 1 is a schematic elevational view of an illustrative electrophotographic printing machine incorporating the apparatus of the present invention therein.

While the present invention will hereinafter be described in connection with a preferred embodiment thereof, it will be understood that it is not intended to limit the invention to that embodiment. On the contrary, it is intended to cover all alternatives, modifications and equivalents as may be included within the spirit and scope of the invention as defined by the appended claims.

Inasmuch as the art of electrophotographic printing is well known, the various processing stations employed in the FIG. 1 printing machine will be shown hereinafter schematically and their operation described briefly with reference thereto.

Referring now to FIG. 1, the electrophotographic printing machine employs a belt 10 having a photoconductive surface 12 deposited on a conductive substrate. Preferably, photoconductive surface 12 is made from a selenium alloy. Conductive substrate 14 is made preferably from an aluminum alloy which is electrically grounded. Belt 10 moves in the direction of arrow 16 to advance successive portions of photoconductive surface 12 sequentially through the various processing stations disposed along the path of movement thereof. Belt 10 is entrained about stripping roller 18, tension roller 20 and drive roller 22. Drive roller 22 is mounted rotatably and in engagement with belt 10. Motor 24 rotates roller 22 to advance belt 10 in the direction of arrow 16. Roller 22 is coupled to motor 24 by suitable means such as a belt drive. Drive roller 22 includes a pair of opposed, spaced edge guides. The edge guides define a space therebetween which determines the desired path of movement of belt 10. Belt 10 is maintained in tension by a pair of springs (not shown) resiliently urging tension roller 20 against belt 10 with the desired spring force. Both stripping roller 18 and tension roller 20 are mounted to rotate freely.

Initially, a portion of belt 10 passes through charging station A. At charging station A, a corona generating device, indicated generally by the reference numeral 26, charges photoconductive surface 12 to a relatively high, substantially uniform potential. High voltage power supply 28 is coupled to corona generating device 26. Excitation of power supply 28 causes corona generating device 26 to charge photoconductive surface 12 of belt 10.

After photoconductive surface 12 of belt 10 is charged, the charged portion thereof is advanced through exposure station B. At exposure station B, an original document 30 is positioned facedown upon a transparent platen 32. Lamps 34 flash light rays onto original document 30. The light rays reflected from original document 30 are transmitted through lens 36 forming a light image thereof. Lens 36 focuses the light image onto the charged portion of photoconductive surface 12 to dissipate selectively the charge thereon. This records an electrostatic latent image on photoconductive surface 12 which corresponds to the informational areas contained with original document 30.

After the electrostatic latent image has been recorded on photoconductive surface 12, belt 10 advances the latent image to development station C. At development station C, a magnetic brush development system, indicated generally by the reference numeral 40, advances developer material into contact with the latent image. Preferably, magnetic brush development system 40 includes two magnetic brush developer rollers 42 and 44. Each roller advances developer material into contact with the latent image. These developer rollers form a brush of carrier granules and toner particles extending outwardly therefrom. The latent image attracts toner particles from the carrier granules forming a toner powder image thereon. Preferably, the developer material is electrically conductive. As successive electrostatic latent images are developed, toner particles are depleted from the developer material. A toner particle dispenser, indicated generally by the reference numeral 46, includes a container 50 storing a supply of toner particles therein. Foam roller 52 disposed in sump 54 beneath container 50, meters toner particles into auger 56. Motor 58 is coupled to auger 56. As motor 58 rotates, auger 56 advances toner particles for discharge into developer housing 48. Energization of motor 58 is regulated by controller 38. A sensor, indicated generally by the reference numeral 60, includes a pair of electrically conductive plates 62 and 64. These plates define a passageway through which developer mixture passes. A substantially transparent prism 66 is secured to plate 62. Plate 62 is electrically biased to attract toner particles thereto. Light source 68 transmits light rays through prims 66 and substantially transparent plate 62 onto the toner particles adhering thereto. The light rays internally reflected through plate 62 and prism 66 are detected by light detector 70. Light detector 79 develops an elecrtrical output signal which is transmitted to controller 38. Controller 38 generates an error signal which actuates motor 58 to dispense toner particles into developer housing 48. Thus, when the quantity of toner particles adhering to plate 62 is beneath a predetermined level, controller 38 actuates motor 58 to discharge additional toner particles into the developer material. The discharging of additional toner particles into the developer material adjusts the developability of the system to the desired level. The detailed structure of sensor 60 will be described hereinafter with reference to FIGS. 2 through 6, inclusive.

With continued reference to FIG. 1, after the electrostatic latent image is developed, belt 10 advances the toner powder image to transfer station D. A sheet of support material 72 is advanced to transfer station D by sheet feeding apparatus 74. Preferably, sheet feeding apparatus 74 includes a feed roll 76 contacting the uppermost sheet of stack 78. Feed roll 76 rotates to advance the uppermost sheet from stack 78 into chute 80.

Chute 80 directs the advancing sheet of support material into contact with photoconductive surface 12 of belt 10 in a timed sequence so that the toner powder image developed thereon contacts the advancing sheet of support material at transfer station D. Transfer station D includes a corona generating device 82 which sprays ions onto the back side of sheet 72. This attracts the toner powder image from photoconductive surface 12 to sheet 72. After transfer, sheet 72 continues to move in the direction of arrow 84 onto a conveyor (not shown) which advances sheet 72 to fusing station E.

Fusing station E includes a fuser assembly, indicated generally by the reference numeral 86, which permanently affixes a transferred powder image to sheet 72. Preferably, fuser assembly 86 comprises a heated fuser roller 88 and a back-up roller 90. Sheet 72 passes between fuser roller 88 and back-up roller 90 with the toner powder image contacting fuser roller 88. In this manner, the toner powder image is permanently affixed to sheet 72. After fusing, chute 92 advances sheet 72 to catch tray 94 for subsequent removal from the printing machine by the operator.

After the sheet of support material is separated from photoconductive surface 12 of belt 10, the residual toner particles adhering to photoconductive surface 12 are removed therefrom at cleaning station F. Cleaning station F includes a rotatably mounted fibrous brush 96 in contact with photoconductive surface 12. The particles are cleaned from photoconductive surface 12 by the rotation of brush 96 in contact therewith. Subsequent to cleaning, a discharge lamp (not shown) floods photoconductive surface 12 with light to dissipate any residual electrostatic charge remaining thereon prior to the charging thereof for the next successive imaging cycle.

It is believed that the foregoing description is sufficient for purposes of the present invention to illustrate the general operation of an illustrative electrophotographic printing machine incorporating the features of the present invention therein.

Referring now to FIG. 2, sensor 60 is disposed in the chamber of developer housing 48 (FIG. 1). A portion of the developer mixture passes between plates 62 (FIG. 1) and 64 (FIG. 1) of sensor 60. Toner particles are attracted from the developer mixture to plate 62 (FIG. 1). Sensor 60 detects the quantity of toner particles adhering thereto and develops an electrical output signal indicative thereof. Controller 38 receives the electrical output signal from sensor 60 and processes it. Controller 38 includes a level detector 98 and a voltage supply 100. Voltage supply 100 is coupled to sensor 60 to furnish the appropriate electrical bias to the conductive layer adhering to plate 62 (FIG. 1) and to the light source and light detector. By way of example, level detector 98 includes logic elements to process the electrical output signal from sensor 60. The logic elements include preferably a suitable discriminator circuit for comparing a reference with the electrical output signal from sensor 60. The discriminator circuit may utilize a silicone control switch which turns on and effectively locks in after an electrical output signal has been obtained having a magnitude greater than the reference level (i.e. set point). The signal from the discriminator circuit changes the state of a flip-flop to develop an output signal therefrom. The output signal from the flip-flop in conjunction with an output signal from the developer unit actuates an AND gate which, in turn, transmits a control signal to toner dispenser motor 58. The control signal also resets the flip-flop. This type of logic circuit is on-off. However, in the alternative, it is possible to utilize proportional circuitry which varies the quantity of toner particles metered to the developer unit as a function of the control signal. This may be achieved by a suitable integrated circuit module for developing a stepped proportional dispensing signal.

Referring now to FIG. 3, plate 62 is substantially transparent having an electrically conductive layer 102 adhering thereto. Preferably, electrically conductive layer 102 is a transparent tin oxide coating which is made by Pittsburgh Plate Glass under the trademark NESA or is made by the Corning Glass Company under the trademark ElectroConductive. Prism 66 is secured to the surface of plate 62 opposed to the surface having conductive layer 102 adhering thereto. Preferably, prism 66 is a right triangular prism with the hypotenuse, i.e. surface 106, secured to the surface of plate 62. The angles of transparent prism 66 opposed from the legs are equal and about 45°. Plate 64 is spaced from and parallel to plate 62 to define a passageway through which developer mixture 108 passes. Magnetic member 110 is positioned to attract at least a portion of the developer material 108 passing between plates 62 and 64 toward plate 62. This further facilitates the attraction of toner particles from the developer mixture toward conductive layer 102 of plate 62.

Voltage supply 100 is coupled to electrically conductive layer 102 so as to electrically bias the surface of plate 62, thereby attracting toner particles from developer mixture 108. Magnet 110 attracts at least a portion of the developer mixture toward plate 62. Thus, magnet 110 diverts a portion of the developer mixture flowing through the passageway between parallel plates 62 and 64 toward plate 62. Light source 68 is preferably a light emitting diode with light detector 70 being a phototransistor. Light emitting diode 68 and phototransistor 70 are coupled to voltage source 100 through suitable circuitry. The characteristics of this circuitry depend upon the type of light emitting diode and phototransistor used. Preferably, the light emitting diode operates in the near infrared region and uses a lens to define the spot. Light emitting diode 68 directs light rays through prism 66 and transparent plate 62. The internally reflected light rays which pass through plate 62 and prism 66 are sensed by phototransistor 70 which, in turn, develops an electrical output signal.

In operation, phototransistor 70 senses the change in internal reflectance. As toner particle deposition occurs on the surface of plate 62, the magnitude of the internally reflected light detected is reduced. Thus, the presence of toner particles on the surface of plate 62 causes a decrease in the detected light intensity which corresponds to a decrease in the internal reflectivity of the surface. The total "internal" reflected radiation field extends beyond the face of plate 62 a distance on the order of a wavelength of light. This is the exponentially decaying evanescent field. Thus, there are two categories of energy coupling through plate 62 and prism 66, one due to the intimate contact of the toner particles with the plate surface and the other due to the toner particles located near the plate surface mediated by the evanescent field. In the first case, the internal reflectivity of the plate and prism is reduced by transmission into the toner particles, characterized by an index of a fraction and an absorption coefficient. The second operates by an evanescent field coupling of energy from the plate surface to the toner particles rather than relying on intimate contact between the surface and the toner particles. It appears that the evanescent field affect dominates to produce the large signal sensitivity that has been found in this sensing apparatus.

Voltage supply 100 provides a low voltage for the light emitting diode and phototransistor as well as a high voltage electrically biasing plate 62. When the polarity of the voltage biasing plate is switched, toner particles are repelled from the surface of plate 62. Thus, one polarity attracts toner particles with the opposite polarity repeling toner particles from plate 62. Toner particles are repeled during the cleaning operation. Positioning of magnetic member 110 further enhances both the attraction mode and the cleaning mode. This is achieved by diverting a portion of the developer mixture flowing between plates 62 and 64 toward plate 62. During the attraction mode, this provides a greater supply of developer mixture closely adjacent to plate 62 so as to facilitate the attraction of toner particles thereto. During the cleaning mode, the diversion of developer material toward plate 62 provides a scrubbing action across the surface thereto to assist in the removal of toner particles therefrom.

Referring now to FIG. 4, there is shown an embodiment of sensor 60 wherein phototransistor 70 and light emitting diode 68 are embedded in prism 66. As illustrated thereat, phototransistor 70 is embedded in prism 66 adjacent a surface thereof opposed from one of the 45° angles, i.e. one leg. Similarly, light emitting diode 68 is embedded in prism 66 adjacent the other surface thereof opposed from the other 45° angle, i.e. the other leg. Preferably, light emitting diode 68 is surrounded by an air space or employs a suitable lens to achieve the desired characteristics of the light rays emitted therefrom, e.g. collimated light rays. The internal angle of incidence of the light source is preferably slightly greater than the critical angle, i.e. greater than 41.5°. In this way, the light rays internally reflected are detected by phototransistor 70 such that the output signal therefrom is maximized. It should also be noted that not only may visible light rays be employed, but longer wavelength radiations such as an infrared light source may also be utilized in this system.

Turning now to FIG. 5, there is shown one embodiment of the transparent conductive layer adhering to the surface of plate 62. As depicted thereat, electrically conductive layer 102 covers the entire surface of plate 62 and is substantially uniform. An electrically conductive layer of this type maximizes the simulation of solid area development. In developing electrostatic latent images on a photoconductive surface, both the solid areas and lines must be developed. Thus, if one wishes to simulate solid areas within the electrostatic latent image, layer 102 may be substantially uniform on plate 62.

Referring now to FIG. 6, an alternate embodiment of electrical layer 102 adhering to plate 62 is depicted thereat. As illustrated in FIG. 6, electrically conductive layer 102 covers only discrete portions or regions of the surface of plate 62 with the other regions being nonconductive. Thus, electrically conductive layer 102 forms a plurality of interdigited conductive regions with the regions adjacent thereto being non-electrically conductive. Nonconductive region 118 is adjacent to conductive regions 120 and 122. Toner particles will only be attracted to the conductive region. When conductive regions 120 and 122 are electrically biased to different potentials, line development is simulated. Alternatively, if conductive regions 120 and 122 are electrically biased to the same potential, solid area development is simulated. Nonconductive region 118 is formed by etching the pattern of conductive regions 120 and 122 on the surface of plate 62.

The availability of detailed developability information from the sensing apparatus of the present invention enables the system to furnish additional toner particles to the developer material as a function of the developability curve. In addition, this information is useful not only for controlling the concentration of toner particles within the developer material, but also for regulating the electrical bias applied to the developer roller. The detailed developability curve information may be used for the addition of two different types of toner particles or toner particles plus an additive to the developer material. Furthermore, the level of charge applied to the photoconductive surface during charging may also be controlled as a function of this information.

It is, thus, clear that the sensing apparatus of the present invention simulates developability within an electrophotographic printing machine to optimize control thereof. Furthermore, the system not only provides a means for controlling the concentration of toner particles within the developer material, but may also provide a technique for regulating charging and the electrical bias applied to the developer roller as well. The utilization of this control scheme optimizes various parameters within the printing machine to automatically account for varying environmental and aging characteristics. Hence, the sensing apparatus of the present invention provides a means whereby significant improvements may be achieved in the quality of copies produced by electrophotographic printing machines.

In recapitulation, it is apparent that the sensing apparatus of the present invention measures the change in internal reflectance to provide a signal indicative of developability. This signal may be employed to control the concentration of toner particles within the developer material, adjust charging and regulate the electrical bias applied to the developer roller, amongst others.

It is, therefore, apparent that there has been provided in accordance with the present invention, an apparatus for sensing developability in an electrophotographic printing machine. This apparatus fully satisfies the aims and advantages hereinbefore set forth. While this invention has been described in conjunction with specific embodiments thereof, it is evident that many alternatives, modifications and variations will be apparent to those skilled in the art. Accordingly, it is intended to embrace all such alternatives, modifications and variations as fall within the spirit and broad scope of the appended claims.

What is claimed is:

1. An apparatus for sensing electrostatically charged particles, including:
    a pair of spaced-apart conductive plates defining a passageway through which a portion of the charged particles flow with at least one of said pair of plates being substantially transparent;
    a member secured to one surface of said transparent plate;
    means for electrically biasing said transparent plate to attract a portion of the particles to the other surface thereof;
    means for tansmitting a beam of energy through said member and said transparent plate with the internal angle of incidence of the beam of energy being greater than the critical angle of incidence of said member; and means for detecting the intensity of the beam of energy internally reflected through said transparent plate and said member.

2. An apparatus according to claim 1, wherein said member includes a substantially transparent prism.

3. An apparatus according to claim 2, wherein said prism is a right triangular prism having equal opposed interior angles.

4. An apparatus according to claim 3, wherein said transparent plate is secured to said prism on the surface thereof opposed from the right angle therein.

5. An apparatus according to claims 2 or 4, wherein said transmitting means includes a light source transmitting light rays through said prism and said transparent plate onto the charged particles adhering thereto.

6. An apparatus according to claim 5, wherein said light source is secured to a surface of said prism other than the surface of said prism having said transparent plate secured thereto.

7. An apparatus according to claim 6, wherein said detecting means includes a light sensor positioned to receive light rays internally reflected through said prism and said transparent plate.

8. An apparatus according to claim 6, wherein said light sensor is secured to a surface of said prism.

9. An apparatus according to claim 8, wherein said transparent plate includes a substantially transparent, electrically conductive layer.

10. An apparatus according to claim 9, wherein said conductive layer is of a substantially uniform area.

11. An apparatus according to claim 9, wherein said conductive layer is arranged in a pattern of conductive and non-conductive regions.

12. An apparatus according to claim 2, further including means for diverting a portion of the charged particles in the passageway between said pair of plates toward said transparent plate.

13. An apparatus according to claim 12, wherein said diverting means includes a magnetic member positioned before said prism in the direction of flow of the charged particles.

14. An apparatus according to claim 2, wherein said detecting means generates a signal indicative of the quantity of charged particles attracted to the surface of said transparent plate.

15. An electrophotographic printing machine of the type having an electrostatic latent image recorded on a photoconductive surface developed with charged particles from a developer mixture, wherein the improvement includes:

a pair of spaced-apart conductive plates defining a passageway through which a portion of the developer mixture flows with at least one of said pair of plates being substantially transparent;

a member secured to one surface of said transparent plate;

means for electrically biasing said transparent plate to attract a portion of the charged particles in the developer mixture to the other surface thereof;

means for transmitting a beam of energy through said member and said transparent plate with the internal angle of incidence of the beam of energy being greater than the critical angle of incidence of said members; and means for detecting the intensity of the beam of energy internally reflected through said transparent plate and said member.

16. A printing machine according to claim 15, wherein said member includes a substantially transparent prism.

17. A printing machine according to claim 16, wherein said prism is a right triangular prism having equal opposed interior angles.

18. A printing machine according to claim 17, wherein said transparent plate is secured to said prism on the surface thereof opposed from the right angle therein.

19. A printing machine according to claims 16 or 18, wherein said transmitting means includes a light source transmitting light rays through said prism and said transparent plate onto the charged particles adhering thereto.

20. A printing machine according to claim 19, wherein said light source is secured to a surface of said prism other than the surface of said prism having said transparent plate secured thereto.

21. A printing machine according to claim 20, wherein said detecting means includes a light sensor positioned to receive light rays internally reflected through said prism and said transparent plate.

22. A printing machine according to claim 21, wherein said light sensor is secured to a surface of said prism.

23. A printing machine according to claim 22, wherein said transparent plate includes a substantially transparent, electrically conductive layer.

24. A printing machine according to claim 23, wherein said conductive layer is of a substantially uniform area.

25. A printing machine according to claim 24, wherein said conductive layer is arranged in a pattern of conductive and non-conductive regions.

26. A printing machine according to claim 16, further including means for diverting a portion of the developer mixture flowing in the passageway between said pair of plates toward said transparent plate.

27. A printing machine according to claim 26, wherein said diverting means includes a magnetic member positioned before said prism in the direction of flow of the developer mixture.

28. A printing machine according to claim 16, wherein said detecting means generates a signal indicative of the quantity of charged particles attracted to the surface of said transparent plate.

* * * * *